United States Patent [19]

Gammill

[11] 4,313,883

[45] Feb. 2, 1982

[54] HALOFUROCHROMONES

[75] Inventor: Ronald B. Gammill, Portage, Mich.

[73] Assignee: The Upjohn Company, Kalamazoo, Mich.

[21] Appl. No.: 201,933

[22] Filed: Oct. 29, 1980

Related U.S. Application Data

[60] Division of Ser. No. 116,322, Jan. 28, 1980, Pat. No. 4,284,569, which is a continuation-in-part of Ser. No. 11,816, Feb. 13, 1979, abandoned.

[51] Int. Cl.$^3$ ............................................ C07D 311/78
[52] U.S. Cl. ................................................... 260/345.2
[58] Field of Search ....................................... 260/345.2

[56] References Cited

U.S. PATENT DOCUMENTS

| | | | |
|---|---|---|---|
| 2,680,119 | 6/1954 | Robertson et al. | 260/345.2 |
| 2,736,727 | 2/1956 | Fourneau | 260/345.2 |
| 2,855,406 | 10/1958 | Dann | 260/345.2 |
| 3,099,660 | 7/1963 | Dann | 260/345.2 |
| 3,483,194 | 12/1969 | Musante et al. | 260/345.2 |

OTHER PUBLICATIONS

Abu–Shady et al., J. Pharm. Belg., 33, 397 (1978).
Schönberg et al., JACS, 11, 5439 (1955).
Mustafa et al., J. Org. Chem., 26, 886 (1961).
Musante et al., Pharmaco (Pavie) Ed. Sci. 15, 81 (1960).
Abu–Shady, U.A.R.J. Pharm. Sci., 11, 283 (1970).
Fabbrini, Ann. Chim. (Rome), 46, 130 (1956).

*Primary Examiner*—Nicky Chan
*Attorney, Agent, or Firm*—William J. Scanlon; Lawrence T. Welch

[57] ABSTRACT

The present invention provides novel halofurochromones, which are useful as antiatherosclerotic agents.

9 Claims, No Drawings

HALOFUROCHROMONES

DESCRIPTION

CROSS REFERENCE TO RELATED APPLICATIONS

This application is a divisional of copending application Ser. No. 116,322, filed Jan. 28, 1980, now U.S. Pat. No. 4,284,569 which is a continuation-in-part of Ser. No. 011,816, filed Feb. 13, 1979, now abandoned.

BACKGROUND OF THE INVENTION

The present invention relates to novel furochromones which are kellin analogs and useful as antiatherosclerotic agents. Most particularly the present invention relates to halofurochromones, the pharmaceutical use and preparation of which is described in appendix A, which is the specification of application Ser. No. 116,322, referred to above.

PRIOR ART

Extensive pharmacological uses for khellin and related substances are known, as indicated above. Khellin analogs are also known in the art, as indicated above, particularly halofurochromone analogs. However, these halofurochromones are all 6-chloromethyl- or 6-iodomethylfurochromones. See Hamed, Abu-Shady, UAR J. Pharm. Sci., 11:283, 1970. Other halofurochromones include 6,7-dihalo-6,7-dihydrofurochromones, see Fabbrini, L., Ann. Chim. (Rome), 46:130 (1956). Alkyl and alkoxy khellin analogs are disclosed in U.S. Pat. Nos. 3,099,660; 2,680,119 and 2,666,766. Other furochromones are disclosed in U.S. Pat. Nos. 3,483,194, 2,855,406 and 2,736,727.

SUMMARY OF THE INVENTION

The present invention particularly provides a furochromone of formula VI

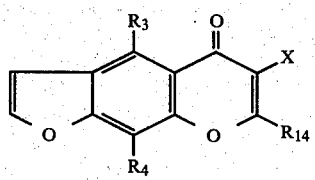

wherein $R_{14}$ is:
(a) hydrogen;
(b) alkyl of one to 8 carbon atoms, inclusive;
(c) alkoxymethyl of 2 to 8 carbon atoms, inclusive;
(d) alkylthioalkyl of 2 to 8 carbon atoms, inclusive;
(e) trifluoromethyl;
(f) phenoxymethyl;
(g) phenylthiomethyl;
(h) phenoxymethyl or phenylthiomethyl substituted by chloro, fluoro, trifluoromethyl, alkyl of one to 3 carbon atoms or alkoxy of one to 3 carbon atoms; or
(i) cycloalkyl of 3 to 10 carbon atoms, inclusive;
wherein one of $R_3$ and $R_4$ is methoxy and the other is methoxy or hydrogen; and
wherein X is chloro, iodo, or bromo. These compounds are useful as antiatherosclerotic agents as described in Ser. No. 116,322.

DESCRIPTION OF THE PREFERRED EMBODIMENTS

The present invention particularly relates to:
6-Bromo-4,9-dimethoxyfurochromone,
6-Bromo-7-methyl-4,9-dimethoxyfurochromone,
6-Chloro-7-methyl-4,9-dimethoxyfurochromone.

APPENDIX A

DESCRIPTION

CROSS REFERENCE TO RELATED APPLICATIONS

The present application is a continuation-in-part of U.S. Ser. No. 011,816, filed Feb. 13, 1979.

TECHNICAL FIELD

The present specification provides methods for use of pharmacologically active substances. Further the present specification provides novel compositions of matter and novel methods of their preparation.

The present specification particularly relates to the use of a known pharmacological agent, khellin, also known as "visamin", and structurally related antiatherogenic furochromones. Chemically, khellin is a furochromone. Furochromones are characterized generally by the structural formula I. Specifically, khellin is the furochromone of formula II, and is trivially named 7-methyl-4,9-dimethoxyfurochromone. Khellin and related furochromones are naturally-occurring substances and have been used in crude form as pharmacological agents for centuries. Khellin is an extract from the plant Ammi visnaga. This plant grows wild in Eastern Mediterranean countries. Aside from khellin, Ammi visnaga is also a source of at least three other known and characterized furochromones, specifically visnagin (formula III), khellinin (formula IV), and ammiol (formula V).

The formula III compound is trivially named 7-methyl-4-methoxy-furochromone the formula IV compound is trivially named 7-glucoyloxymethyl-4-methoxyfurochromone, the formula XIV compound is trivially named 7-hydroxymethyl-4,9-dimethoxyfurochromone and the formula V compound is trivially named 7-hydroxymethyl-4,9-dimethoxyfurochromone.

In ammi visnaga, khellinin and khellin are ordinarily present in approximately equal amounts, while visnagin and ammiol are present only as minor or insignificant constituents. Moreover, khellinin has been reported to be of no therapeutic interest, notwithstanding the wide variety of known therapeutic uses for khellin. See, for example, Anrep, G. V., et al., "The Coronary Vasodilator Action of Khellin", in the American Heart Journal 37:531–542 (1949). Anrep, et al., also report the biological action of visnagin as being similar to that of khellin, but khellinin is somewhat less potent than khellin.

As indicated above, khellin exhibits a wide variety of pharmacological actions, rendering this compound a useful agent for numerous pharmacological purposes. For a comprehensive, but somewhat dated, review of the chemistry and physiological action of khellin-related products, see the reports of Huttrer, C. P., et al., Chem. Revs. 48:543–79 (1951) and Aubertin, E., J. Med. Bordeaux 127:819–23 (1950).

One principal action of khellin is its ability to induce relaxation of smooth muscle tissues. Particularly, khellin is known as a potent dilator of coronary blood vessels. This potent coronary vasodilator activity of khellin renders the compound useful in the treatment of angina pectoris and other diseases characterized by coronary artery insufficiency. For a description of the use of khellin in the treatment of such diseases, see Osher, H. L., et al., "Khellin in the Treatment of Angina Pectoris", The New England Journal of Medicine 244:315 (1951). Also the effects of enteric-coated khellin on coronary artery insufficiency is reported by Best, M. M., et al., J. Med. Sci. 222:35–9 (1951). The ability of khellin to relax smooth muscle also extends to gastrointestinal smooth muscle where khellin has been demonstrated to inhibit peristalsis, thus indicating antidiarrhetic potential. See Ramond-Hamet, Compt. Rend. 238:1624–6 (1954). Khellin may also be useful for the treatment of gastrointestinal disorders exhibiting a spasmotic component, as suggested by Anrep, G. V., et al., cited above. Further the antispasmotic effects of khellin on the urethra is reported by Colombo, G., et al., Arch. Sci. Med. 97:71 (1954) and Monlorse, W., et al., Presse Med. 63:81 (1955).

The antispasmotic action of khellin also extends to bronchial smooth muscle, rendering khellin useful in the treatment of asthma and other hypoxic pulmonary diseases. In this regard, see Silber, E. N., et al., "The Effect of Khellin on Cardio-Pulmonary Function in Chronic Pulmonary Disease", published in 1951; Anrep, G. V., et al., "Therapeutic Uses of Khellin", The Lancet, April 26, 1947, pages 557–8.

Khellin has also been reported to exert a hypotensive effect in humans by Jordan, H., Arzneimittel-Forsch 8:141–3 (1958), and 7:82–5 (1957). An additional account of the hypotensive effect of khellin is provided by Lian, C., et al., Acta. Cardiol. (Brussels) 5:373–88 (1950). With respect to overall cardiac effects, however, khellin has been reported to exert a cardiac depressive activity, while khellinin is reportedly a cardiac stimulant. In this regard see Samaan, K., et al., J. Roy. Egypt Med. Assoc. 33:953 (1950) and J. Pharm. Pharmacol. 1:538–44 (1949).

In addition to its effect on gastrointestinal smooth muscle reported above, khellin is also known as a gastric antisecretory and antiulcer agent. In this regard, the gastric antisecretory activity of khellin is reported by Hans, M. J., et al., Compt. Rend. Soc. Biol. 150:1806–7 (1956) and 150::598–9 (1956).

Numerous other miscellaneous properties of khellin are also reported. For an account of its anthelminic activity see Boytop, O. T., Folia, Pharm. (Turkey) 1:48–9 (1949). For an account of the CNS depressant activity of khellin see Chen, G., Proc. Soc. Expetl. Biol. Med. 78:306–7 (1951). For an account of the cytostatic activity of khellin see Apfsel, C. A., Deut. Med. Wochschr. 80:414–16 (1955). Finally, the spermacidal action of khellin is reported by Swayne, V. R., et al., Aman, J. Pharm. 125:295–8 (1953).

Atherosclerosis in mammals is a disease characterized by the deposition of atherosclerotic plaque on arterial walls. While atherosclerosis exhibits many varied forms and consequences, typical consequences of atherosclerotic diseases include angina pectoris, myocardial infarction, stroke and transient cerebral ischemic attacks. Other forms of atherosclerotic diseases include certain peripheral vascular diseases and other ischemias (e.g., bowel and renal).

Medical science now recognizes that certain forms of atherosclerosis may be preventable or reversible. Agents capable of preventing or reversing atherosclerosis are characterized as exhibiting antiatherosclerotic activity. Since serum lipids have a recognized association with atherogenesis, an important class of antiatherosclerotic agents are those with serum lipid-modifying effects. Serum lipids implicated in atherogenesis include serum cholesterol, serum triglycerides, and serum lipoproteins.

With respect to serum lipoproteins, at least three different classes of these substances have been characterized: high density lipoproteins (HDL's), low density lipoproteins (LDL's), and very low density lipoproteins (VLDL's). HDL's are often referred to as alphalipoproteins, while LDL's and VLDL's are referred to as betalipoproteins. The enhancement to HDL levels (hypeealphalipoproteinemic activity) is postulated to have direct antiatherosclerotic effects. See Eaton, R. P., J. Chron. Dis. 31:131–135 (1978). In contrast, agents which reduce serum LDL's and serum VLDL's (hypobetalipoproteinemic agents) are also associated with antiatherogenic effects. See Haust, M. D., "Reaction Patterns of Intimal Mesenchyme to Injury and Repair in Atherosclerosis:, Adv. Exp. Med. Biol. 43:35–57 (1974), which postulates that serum LDL is a factor in atherosclerotic lesion formation.

Numerous animal models have been developed for assessing antiatherogenic activity. Principal among these are models for assessing hypobetalipoproteinemic activity in the rat, antiatherosclerotic activity in the Japanese quail, and lipoprotein modifying activity in the monkey. For a description of the operation of the hypobetalipoproteinemic rad model, refer to the known methods of Schurr, P. E., et al., "High Volume Screening Procedure for Hypobetalipoproteinemia Activity in Rats", Adv. Exp. Med. Biol. 67: Atherosclerotic Drug Discovery, pp. 215–229, Plenum Press (1975). For a description of the Japanese quail model, see Day, C. E., et al., "Utility of a Selected Line (SEA) of the Japanese Quail (Coturnic Coturnix japonica) for the Discovery of New Anti-Atherosclerosis Drugs", Laboratory Animal Science 27:817–821 (1977).

A suitable primate model for assessing antiatherosclerotic activity of chemical compounds is found in the cynomolgus monkey. In these animals base-line values for VLDL's, LDL's, and HDL's can be determined by controlling diet over a period of several weeks and sampling plasma daily. After establishing control values, the effects of drug treatment are assessed by administering by gavage with a predetermined series of doses of test compounds for a similar period (e.g., two weeks).

4,9-Dimethoxyfurochromones are known in the art. Such known compounds include 7-ethyl, 7-phenyl, 7-propyl, and 7-ethoxycarbonyl analogs described by Shonberg, A., et al., JACS 72:1611–17 (1950); 7-γ-pyridyl analogs, described by Shonberg, A., JACS 77:5439 (1955); 7-furanyl analogs, described by Musante, C., et al., Pharmaco. (Pavie) Ed. Sci. 15:81–94 (1960); 7-carboxyaldehyde analogs, described by Mustafa, A., et al., J. Org. Chem. 26:86 (1961). Also, 6-substituted-4,9-dimethoxyfurochromones are known. See, for example, the compounds described by Hamed, Abu-Schady, UAR J. Pharm. Sci. 11:283 (1970).

4-Methoxy-7-aminomethylenefurochromones are also known in the art. See Abm-Shady, H., et al, J. Pharm. Belg. 33:397 (1978).

PRIOR ART

Extensive pharmacological uses for khellin and related substances are known, as indicated above. Khellin analogs are also known in the art, as indicated above, particularly halofurochromone analogs. However, these halofurochromones are all 6-chloromethyl- or 6-iodomethylfurochromones. See Hamed, Abu-Shadz, UAR J. Parm. Sci., 11:283, 1970. Other halofurochromones include 6,7-dihalo-6,7-dihydro furochromones, see Fabbrini, L., Ann., Chim. (Rome), 46:130 (1956).

SUMMARY OF THE INVENTION

The present specification particularly provides methods of treatment, including:

(1) a method of treating or preventing atherogenic hyperlipoproteinemia in a mammal suffering from or susceptible to the development of an atherosclerotic disease which comprises:

administering systemically to said mammal in amount of a khellin-related product effective to significantly reduce levels of atherogenic serum lipoproteins;

(2) a method of reversing atherosclerotic lesions in a mammal which comprises:

administering systemically to said mammal an amount of khellin-related product effective to significantly reduce levels of atherogenic serum lipoproteins or selectively enhance levels of antiatherogenic serum lipoproteins;

(3) a method of treating a mammal suffering from or susceptable to the development of an atherosclerotic disease which comprises:

administering systemically to said mammal an amount of khellin-related product effective to significantly reduce levels of atherogenic serum lipoproteins or enhance selectively levels of antiatherogenic serum lipoproteins; and (4) a method of treating or preventing atherogenic hypolipoproteinemia in a mammal suffering from or susceptible to the development of an atherosclerotic disease which comprises:

administering systemically to said mammal an amount of a khellin-related product effective to significantly enhance levels of antiatherogenic serum lipoproteins.

Moreover, the present specification further discloses novel organic compounds, particularly:

a furochromone of formula VI
wherein A is:
(a) $-CH=CR_{13}-$;
(b) $-CX=CR_{14}-$;
(c) $-CHR_{11}=C(CH_3)-$;
(d) $-CH_2-CHR_{14}-$;
(e) $-CHR_{17}-$;

wherein $R_{11}$ is $-CH_2SR_{10}$, or $-CH_2SOR_{10}$, or $-CH_2(SO_2)R_{10}$, wherein $R_{10}$ is alkyl of one to 5 carbon atoms, inclusive;

wherein $R_{14}$ is:
(a) hydrogen;
(b) alkyl of one to 8 carbon atoms, inclusive;
(c) alkoxymethyl of 2 to 8 carbon atoms, inclusive;
(d) alkylthioalkyl of 2 to 8 carbon atoms, inclusive;
(e) trifluoromethyl;
(f) phenoxymethyl;
(g) phenylthiomethyl;
(h) phenoxymethyl or phenylthiomethyl substituted by chloro, fluoro, trifluoromethyl, alkyl of one to 3 carbon atoms or alkoxy of one to 3 carbon atoms; or
(i) cycloalkyl of 3 to 10 carbon atoms, inclusive;

wherein $R_{13}$ is:
(a) isopropyl;
(b) alkyl of 4 to 8 carbon atoms, inclusive;
(c) alkoxymethyl of 2 to 8 carbon atoms, inclusive;
(d) alkylthiomethyl of 2 to 8 carbon atoms, inclusive;
(e) trifluoromethyl;
(f) phenoxymethyl;
(g) phenylthiomethyl;
(h) phenoxymethyl or phenylthiomethyl substituted by chloro, fluoro, trifluoromethyl, alkyl of one to 3 carbon atoms, or alkoxy of one to 3 carbon atoms;
(i) cycloalkyl of 3 to 10 carbon atoms, inclusive;
(j) $-CH_2-S-R_{10}$, $-CH_2-SO-R_{10}$, or $-CH_2SO_2-R_{10}$, wherein $R_{10}$ is alkyl of one to 5 carbon atoms, inclusive; or
(k) $-CH_2NR_8R_9$, wherein $R_8$ and $R_9$ are hydrogen, alkyl of one to 12 carbon atoms, inclusive, or alkyl or 6 to 12 carbon atoms, inclusive, being the same or different, or wherein $R_8$ and $R_9$, taken together with N, form a saturated or unsaturated heterocyclic amine ring consisting of from 2 to 7 carbon atoms, inclusive, and zero, one, or 2 additional hetero atoms, with the proviso that said heterocyclic amine ring contains 4 to 8 atoms in the ring, said additional hetero atoms being selected from the group consisting of oxygen, nitrogen, and sulfur, said heterocyclic amine ring being optionally substituted by alkyl of one to 4 carbon atoms, inclusive, alkylthiomethyl or alkoxymethyl of 2 to 8 carbon atoms, inclusive, hydroxyalkyl of one to 4 carbon atoms, inclusive, or phenyl, with the proviso that $R_{13}$ is $-CH_2NR_8R_9$ only when $R_4$ is methoxy;

wherein $R_{17}$ is hydrogen or alkyl of one to 8 carbon atoms, inclusive;

wherein one of $R_3$ or $R_4$ is methoxy and the other is methoxy or hydrogen;

wherein X is chloro, iodo, or bromo;

wherein $R_{20}$ and $R_{21}$, taken together form an oxo group or wherein one of $R_{20}$ and $R_{21}$ is hydroxy and the other is hydrogen, with the proviso that $R_{20}$ and $R_{21}$ taken together are an oxo group only when A is not $-CH_2-CHR_{14}$ and one of $R_{20}$ and $R_{21}$ is hydroxy only when A is $-CH_2-CHR_{14}-$;

and the pharmacologically acceptable acid addition salts when $R_{14}$ is $-CH_2NR_8R_9$.

Accordingly the present specification provides a 7-substituted furochromone when A is $-CH=CR_{13}-$ in formula VI, i.e., the formula VII compound; a 6-halofurochromone when A is $-CX=CR_{14}-$ in formula VI, i.e., the formula VIII compound; a 6-S-substituted furochromone when A is $-CR_{11}=C(CH_3)-$ in formula VI, i.e., the formula IX compound; a 5-hydroxy-6,7-dihydrofurochromone when A is $-CH_2-CHR_{14}-$ in formula VI, i.e., the formula X compound; and a benzodifuran when A is $-CHR_{17}-$ in formula VI, i.e, the formula XI compound.

The novel furochromones of formula VI and the khellin-related products of Ammi visnaga are all characterized by pronounced antiatherogenic activity, rendering these compounds useful in the treatment and prophylaxis of atheroscherosis, atherogenic hyperlipoproteinemia (i.e., hypobetalipoproteinemia) and atherogenic hypolipoproteinemia (i.e., hypoalphalipoproteinemia), and the untoward consequences thereof. While these compounds exhibit this useful pharmacological activity in both mammalian and non-mammalian species, the use of these compounds in mammals, particularly humans, represents the intendment of the disclosure herein.

The mammals susceptible to the development of atherosclerotic diseases and the untoward consequences thereof are particularly those physically asymptomatic patients manifesting one or more risk factors known to predispose one to disease development. Such risk factors are high serum cholesterol and serum triglycerides, hypertension, obesity, diabetes, and genetic predisposition. Mammals manifesting two or more risk factors are deemed to be especially susceptible to atherosclerotic diseases. The khellin-related products and furochromones of formula VI all exhibit pronounced oral pharmacologic activity. Accordingly, in using these compounds for the instant purposes, an oral route of administration, either by conventional oral dosage forms or by mixture with food or feed, represents the preferred method of their systemic administration. Alternatively, however, these compounds may be administered by other convenient routes of administration whereby systemic activity is obtained. These other routes of administration would, accordingly, include rectal, vaginal, subcutaneous, intravenous, and like routes.

In humans, the preferred route of administration is oral, in the form of capsules or tablets containing the khellin-related product or formula VI furochromone. Methods for the preparation of such oral dosage forms are known in the art. See, for example, the known formulations for khellin in the references hereinbefore described.

In order to obtain the instant pharmacologic activity of the antiatherogenic compounds in accordance with the instant specification, the patient or animal being treated must be given periodic doses of the khellin-related product or formula VI furochromone in amounts effective to reduce atherogenic serum lipoproteins (e.g., betalipoproteins) or selectively enhance levels of antiatherogenic serum lipoproteins (e.g., enhancing alphalipoprotein levels, while supporessing, or at least unaffecting, betalipoprotein levels). Such effective dosages are readily determined by methods known in the art. For example, small daily doses of the khellin-related product or formula VI furochromone (e.g., 50–100 mg) may be administered initially with higher succeeding doses until levels of atherogenic or antiatherogenic serum lipoproteins are favorably affected. By this regimen, a compound is administered initially at doses as low as about 50 mg per patient per day, with increasing doses up to about 200 mg per patient per day. In the event the antiatherogenic response in a patient being treated at a dose of 200 mg per day is insufficient, higher doses are also contemplated in accordance with the present disclosure, providing patient tolerance permits further increases in dose.

While the preferred dosage regimen is with single daily dosing of patients, also preferred for obtaining more uniform serum levels of drug are multiple dosages per day (e.g., up to 4–6 times daily). Accordingly, when 4 daily doses of drug are to be administered, each such dose may be about 50 mg per patient per dose (200–300 mg per patient per dose), or higher depending on tolerance.

Similar doses are employed in non-human mammals, e.g., 1–5 mg/kg/day.

The khellin-related products referred to above are the antiatheroscherotically active substances of Ammi visnaga and specifically include the compounds of formulas II-V.

The novel formula VII 7-substituted furochromones are substituted at the C-7 position by $R_{13}$. $R_{13}$ has preferred values which are the same as $R_{14}$, discussed below, and $-CH_2NR_8R_9$.

The novel formula VIII 6-halofurochromones are such by virtue of the substitution of halogen (chloro, bromo or iodo) for hydrogen at the C-6 position of the skeletal structure for khellin. These 6-halofurochromones are also optionally substituted by $R_{14}$ at the C-7 position, for example, by alkyl, alkoxymethyl, alkylthiomethyl, trifluoromethyl, phenoxymethyl, phenylthiomethyl, or cycloalkyl. Among these various $R_{14}$ substituents, preferred compounds are those wherein $R_{14}$ is hydrogen, lower alkyl (most especially methyl), methoxymethyl, methylthiomethyl, trifluoromethyl, phenoxymethyl, phenythiomethyl, or hydroxymethyl. Of the above, most especially preferred are the compounds wherein $R_{14}$ is hydrogen or methyl.

The novel formula IX 6-S-substituted furochromones are substituted by $R_{11}$ at the C-6 position by alkylthiomethyl, alkylsufinylmethyl, or alkylsufonylmethyl. Among these various substituents, preferred compounds are those wherein $R_{11}$ is methylthiomethyl.

These formula X 5-hydroxy-6,7-dihydro-furochromones are substituted at the C-7 position by $R_{14}$, whose preferred values are described above.

Finally, benzodifurans of Formula XI are substituted at the C-6 position by $R_{17}$. $R_{17}$ is hydrogen or alkyl. Among the various substituents at $R_{17}$, preferred compounds are where $R_{17}$ is hydrogen.

Examples of alkyl of one to 8 carbon atoms, inclusive, are methyl, ethyl, propyl, butyl, pentyl, hexyl, heptyl, octyl, and isomeric forms thereof.

Examples of alkoxymethyl of 2 to 8 carbon atoms, inclusive, are methoxymethyl, ethoxymethyl, propoxymethyl, butoxymethyl, pentoxymethyl, hexoxymethyl, and heptoxymethyl, and isomeric forms thereof.

Examples of alkylthiomethyl are methylthiomethyl, ethylthiomethyl, propylthiomethyl, butylthiomethyl, pentylthiomethyl, hexythiomethyl, and heptylthiomethyl.

Examples of cycloalkyl of 3 to 10 carbon atoms, inclusive, are cyclopropyl, cyclobutyl, cyclopentyl, cyclohexyl, cycloheptyl, and cyclodecyl.

Examples of alkyl of one to five carbons are methyl, ethyl, propyl, butyl and pentyl and isomeric forms thereof.

Examples of alkyl of one to three carbons are methyl, ethyl, propyl, n-propyl, and isomeric forms thereof.

Examples of aryl of 6 to 12 carbon atoms, inclusive, are phenyl, α-naphthyl, β-naphthyl, m-methylphenyl, p-trifluoromethylphenyl, and the like.

Examples of heterocyclic amines corresponding to heterocyclic amine rings according to $-NR_8R_9$ are:
thiazolidine,
3-piperidine methanol,
2-piperidine methanol,
piperadinic acid,
3-piperidine ethanol,
2-piperidine ethanol,
1-piperazinepropanol,
p-piperazinoacetoxyphenone,
4-phenyl-1,2,3,6-tetrahydropyridine,
4-phenylpiperidine,
proline,
3-pyrolidinol,
tetrahydrofurfurylamine,
pyrrolidimethanol,
3-pyrroline,
thiazolidine-4-carboxylic acid, thromorpholine,
nipecstamide,
morpholine,
2-methylpiperidine,
3-methylpiperidine,
4-methylpiperidine,
N-methylpiperazine, and
1-methylhomopiperazine.

The Charts A-F herein describe methods by which the novel formula VI furochromones are prepared. With respect to these Charts X, $R_3$, $R_4$, $R_8$, $R_9$, $R_{10}$, $R_{11}$, $R_{13}$, $R_{14}$, and $R_{17}$ are as defined above.

The various novel 6-halofurchromones disclosed herein, including intermediates therefor, are all prepared by methods described in Charts A and B. With respect to these Charts, $R_{12}$ is $R_{13}$ or $R_{14}$, but is other than hydrogen. X is chloro, bromo or iodo.

With respect to Chart A, the formula XXI compound, khellin or 4 or 9-desmethoxy-khellin is transformed to the formula XXII methylketone by hydrolysis under basic conditions. For example, aqueous potassium hydroxide at elevated temperatures is employed in this transformation in accordance with methods known in the art. See E. Spath and W. Gruber, Chem. Ber. 71:106 (1938).

Thereafter, the formula XXII benzofuranol is transformed to the formula XXIII β-diketone by a Claisen condensation with a carboxylic acid ester, wherein the carboxylic acid residue corresponds to the keto group being attached to the formula XXIII product. Accordingly, there is employed in the preparation of the formula XXIII compound a carboxylic acid ester of the formula $R_{12}COOR_2$, wherein $R_2$ is the ester residue (e.g., preferable a simple alkyl ester such as methyl or ethyl). The reaction proceeds conveniently in an organic solvent in the presence of sodium hydride, followed by treatment with alcoholic hydrochloric acid. Ordinarily, use of three of four equivalents of sodium hydride and two or three equivalents of the carboxylic acid ester per equivalent of formula XXII starting material is preferred. Further, the reaction proceeds in the minimum amount of the organic solvent necessary to solubilize the reactants. Ordinarily, an aprotic polar solvent such as tetrahydrofuran is conveniently employed. However, in preparing the formula XXIII product $R_{12}$ is other than a low molecule weight (sterically small) residue; the ester itself, $R_{12}COOR_2$, is employed as the reaction diluent.

In the production of the formula XXIV compound, the formula XXIII intermediate therefore is ordinarily not isolated, but rather directly subjected to an acid-catalyzed cyclodehydration to yield the formula XXIV furochromone. This cyclodehydration ordinarily proceeds in the presence of a mineral acid in an organic solvent, such as an alkanol (e.g., hydrochloric acid in methanol). However, in preparing the formula XXIV compound where $R_{12}$ is trifluoromethyl, the chlorinated hydrocarbons (e.g., chloroform) represent preferred reaction diluents.

The formula XXV compound is then prepared from the formula XXIV compound by decyclization with pyrrolidine. The reaction proceeds in the presence of several equivalents of pyrrolidine per equivalent of formula XXIV compound at elevated temperature (e.g., refluxing methanol).

Optionally the formula XXIII compound is transformed directly to the formula XXV compound by methods and reagents employed in the above transformation of the formula XXIV compound to the formula XXV compound. This optional method is preferred only when $R_{12}$ is sterically bulky.

Thereafter, the formula XXVI halogenated product is recovered by first halogenation of the formula XXV compound by addition of the molecular halogen (e.g., bromine in chloroform), followed by hydrolysis to yield the formula XXVI 6-halofurochromone. With regard to the halogenation step, other conventional sources of halogen are alternatively employed, e.g., the positive halogen sources such as the hypochlorites. With regard to the latter reaction, the addition of water to the halogenated product effects the desired hydrolysis and cyclodehydration.

When $R_{12}$ in Chart A is methyl, the formula XXVI compound is prepared directly from the formula XXI compound via the formula XXV pyrrolidyl intermediate.

Chart B provides a method whereby the 6-halofurochromones disclosed herein wherein $R_{13}$ is hydrogen (i.e., the formula XXXIII compound) is prepared from the formula XXXI benzofuranol.

In accordance with Chart B the formula XXXI compound is treated with N,N-dimethylformamide dimethylacetal at elevated temperature to yield the formula XXXII enaminoketone. Thereafter, the formula XXXIII compound is prepared from the formula XXXII compound by the method described in Chart A for the preparation of the formula XXVI compound from the formula XXV compound.

Chart C provides a preferred method whereby the formula XLI compounds of Chart A wherein $R_{12}$ is —$CH_2NR_8R_9$ are prepared.

In accordance with the procedure of Chart C, the formula XLI compounds of Chart A wherein $R_{12}$ is —$CH_2$—S—$CH_3$ are employed as the formula XLI starting material. This formula XLI compound is then transformed to the formula XLII compound by treatment with methyl iodide in a chlorinated hydrocarbon, i.e., dichloromethane. The formula XLII compound thusly prepared is then transformed to the formula XLIII compound by treatment with the amine corresponding to the formula XLIII compound.

Chart D provides a method whereby the formula LI compound, prepared according to Chart A (formula XXIV), is transformed to the various 6-S-substituted furochromones of formulas LIII and LIV.

The formula LI compound is first transformed to the formula LII compound by treatment with methylfluorosulfonate flouride ($CH_3OSO_2F$). The resulting sulfonium fluorosulfate (formula LII) is then transformed to the formula LIII compound by treatment with base (e.g., potassium hydroxide or potassium t-butoxide. The reaction proceeds convienty at ambient temperature in a suitable organic solvent (e.g., tetrahydrofuran and water).

The formula LIII furochromone thusly prepared is then optionally oxidized to the formula LIV sulfinyl or sulfonyl compound by methods known in the art. For example, the oxidation employs m-CBPA (metachloroperbenzoic acids) in a chlorinated hydrocarbon solvent (e.g., dichloromethane).

Chart E provides a method whereby the formula LXI 6-bromofurochromone, prepared according to Chart B (the formula XXXIII compound) is transformed to the formula LXIV benzodifuran.

With respect to Chart E, $R_{31}$ and $R_{32}$ are defined such that $NHR_{31}R_{32}$ represents a primary or secondary amine (e.g., pyrrolidine).

The formula LXII compound of Chart E is prepared from the formula LXI compound by reaction with a primary or secondary amine, i.e., $NHR_{31}R_{32}$, in the presence of methyl cyanide and potassium carbonate.

The resulting formula LXII compound is then treated with concentrated mineral acid (e.g., 6 N hydrochloric acid), to yield the formula LXIII product.

This product is optionally alkylated to yield the formula LXIV compound by conventional methods, e.g., by treatment with the corresponding alkyl halide in the presence of base.

Chart F provides a method whereby the formula LXXI compound prepared according to Chart A (formula XXIV) is transformed to the formula LXII and LXIII 5-hydroxy-6,7-dihydro-furochromone products.

The formula LXXI compound is transformed to the formula LXXII compound by reduction. The preferred method of reduction is by treatment of the formula LXXI compound with a borohydride reducing agent, especially sodium borohydride. The formula LXXII compound is then epimerized at the C-5 position to the formula LXXIII compound by methods known in the art for epimerization of hydroxyl groups. By one such method, the formula LXXII compound is transformed to its alkyl or aryl sulfonate by reaction with the corresponding alkyl or aryl sulfonyl chloride in an amine solvent (e.g., pyridine). There is thusly prepared, for example, the mesylate or tosylate corresponding to the formula LXXII compound. Thereafter, the epimerization is completed by reaction of the sulfonate with tetra-n-butyl ammonium acetate followed by treatment with a deacylating agent (e.g., potassium methoxide in methanol). See Baker, R., et al., JACS 1605:1965 or Corey, E. J., et al., Chemical Communication 16:658 (1975).

According to the procedures described by the charts above, there are prepared each of the various furochromones of the present invention.

Pharmacologically acceptable acid addition salts described in the specification are prepared by neutralization of the free base with the appropriate amount of inorganic or organic acid, examples of which are hydrochloric, hydrobromic, sulfuric, nitric, phosphoric, acidic, lactic, benzylic, salicyclic, glyolic, succinic, tartaric, maleic, malic, tymoic, cyclohexenesulfamic, citric and methanesulfonic acids and like acids. The neutralization can be carried out by a variety of procedures known to the art to be generally useful for the preparation of amine acid addition salts. The choice of most suitable procedure will depend on a variety of factors including convenience of operation, and particularly the solubility characteristics of the particular free base, the acid and the acid addition salt. If the acid is soluble in water, the free base can be dissolved in water containing an equivalent amount of the acid and thereafter the water can be removed by evaporation. In some instances, the salt precipitates from the aqueous solution, particularly when cooled and evaporation is not necessary. If the acid is soluble in a relatively non-porous solvent, for example, diethyl ether or diisopropyl ether, separate solutions of the acid and free base and such a solvent can be mixed in equal amounts whereupon the acid addition salt will usually precipitate because of its relatively low solubility in the non-porous solvent. Alternatively, the free base can be mixed with an equivalent amount of the acid in the presence of a solvent of moderate polarity, for example, a lower alkanol, lower alkanone, or a lower alkyl ester of a lower alkanoic acid. Examples of these solvents are ethanol, acetone, ethyl acetate, respectively. Subsequent admixture of the resulting solution of acid addition salt with a solvent of relatively low polarity, for example, diethyl ether or hexane, will usually cause precipitation of the acid addition salt.

DESCRIPTION OF THE PREFERRED EMBODIMENTS

The preparation of the novel furochromones of the instant specification is readily understood by the following examples:

Example 1—6-Hydroxy-4,7-dimethoxy-5-benzofuranyl methyl ketone (Formula XXI compound of Chart A).

To a stirred solution of potassium hydroxide (193.2 g) in 1.5 l of water, heated to 75° C., is added 300 g of khellin (formula XXI) in 50 g portions over a period of 30 minutes. When khellin addition is complete, the resulting mixture is then heated to reflux for 2 hr and thereafter cooled to ambient temperature. Concentrated hydrochloric acid (300 ml) is then added to the cooled solution and the resulting precipitate is collected by filtration and dried at ambient temperature in a vacuum for 18 hr. The resulting crude yellow solid is then recrystallized from one liter of methanol, yielding 251 g of pure title product. Melting point is 99°–100° C. Silica gel TLC Rf is 0.60 is hexane and ethyl acetate (1:1). Infrared absorptions are observed at 3160, 3140, 1700, 1695, 1680, 1620, 1590, 1550, 1300, 1265, 1150, 1075, and 1060 cm$^{-1}$. NMR absorptions are observed at 7.52, 6.91, 4.15, 4.05, 2.72, and 13.06$\delta$ (deuterochloroform solvent). The mass spectrum exhibits peaks at 236, 221, 206, 203, 191, 175, 163, and 119. Carbon:hydrogen ratio is 60.65:5.15.

Example 2—7-Methoxymethyl-4,9-dimethoxyfurochromone (Formula XXIV of Chart A: $R_3$ and $R_4$ are both methoxy and $R_{12}$ is methoxymethyl)

To sodium hydride (20.1 g of a 50% dispersion in oil) and tetrahydrofuran (20 ml freshly distilled from lithium aluminum hydride), combined under a nitrogen atmosphere to form a slurry, are added dropwise a mixture of the formula XXII product of Example 1 (20 g), methyl methoxyacetate (26.4 g) and dry tetrahydrofuran (50 ml). after the addition is complete (1.5 hr) the reaction mixture is then heated on a steam bath for 15 min and cooled to ambient temperature. Thereupon excess sodium hydride is destroyed by careful addition of ice and water (300 ml). Washing with diethyl ether (600 ml) yields an arqueous layer which is diluted with methanol (100 ml) and concentrated hydrochloric acid (75 ml). This mixture is then refluxed for 45 min and thereupon allowed to cool to ambient temperature. Upon extraction with methylene chloride (600 ml) the organic extracts are dried and concentrated under reduced pressure to yield a solid (26.2 g). Recrystallization from methanol yields 18.33 g of pure title product. Melting point is 116°–117° C. Silica gel TLC Rf is 0.57 in ethyl acetate. Infrared absorptions are observed at 3140, 3120, 1665, 1645, 1620, 1550, 1485, 1370, 1360, 1125, 1105, 1075, 1060, 855, and 870 cm$^{-1}$. NMR absorptions are observed at 7.66, 7.02, 6.30, 4.40, 4.21, 4.04, and 3.51$\delta$ (deuterochloroform). The mass spectrum exhibits peaks at 290, 275, 261, 246, 219, 201, and 287. The carbon:hydrogen ratio is 61.96:5.03.

Following the procedure of Example 2, but employing in place of methyl methoxyacetate corresponding methyl alkoxyacetates there are prepared the various formula XXIV 7-alkoxymethylfurochromones.

EXAMPLE 3—7-Methylthiomethyl-4,9-dimethoxyfurochromone
(Formula XXIV of Chart A: $R_3$ and $R_4$ are both methoxy and $R_{12}$ is methylthiomethyl)

Following the procedure of Example 2, but employing ethyl 2-(methylthio)acetate, 56.5 g, in place of methyl methoxyacetate, there if prepared from the title product of Example 1 (50 g) 47.0 g of pure title product as a tan solid. Melting point is 148°–150° C. Silica gel TLC Rf is 0.63 is ethyl acetate. Infrared absorptions are observed at 1650, 1625, 1545, 1480, 1380, 1125, 1070, 1060, 845, and 760 cm$^{-1}$. NMR absorptions are observed at 7.19, 7.05, 6.18, 4.2, 4.05, 3.60, and 2.25$\delta$ (deuterochloroform solvent). The mass spectrum exhibits peaks at 306, 291, 277, 259, 241, 231, 216, and 201. Carbon:hydrogen:sulphur ratio is 58.87:4.76:10.62.

Following the procedure of Example 3, but substituting the appropriate methyl or ethyl 2-(alkylthio)acetate in place of ethyl 2-(methyl)acetate, there are prepared the corresponding formula XXIV compounds wherein $R_{12}$ is alkylthiomethyl.

Example 4—7-Phenylthiomethyl-4,9-dimethoxyfurochromone
(Formula XXIV of Chart A: $R_3$ and $R_4$ are both methoxy and $R_{12}$ is phenylthiomethyl)

To a slurry of sodium hydride (32.44 g of a 50 percent dispersion in oil) and tetrahydrofuran (25 ml freshly distilled from lithium aluminum hydride) under a nitrogen atmosphere is added a mixture of the title product of Example 1 (40.0 g), methyl 2-(phenylthio)acetate (46.2 g) and tetrahydrofuran (75 ml). After addition is complete (1 hr) the resulting mixture is then cooled to ambient temperature and carefully quenched (sodium hydride destroyed) with water, 150 ml. The resulting mixture is then washed with diethyl ether (800 ml) and the resulting aqueous solution is diluted with methanol (300 ml) and concentrated hydrochloric acid (200 ml). After refluxing for 3 hr, the solution is then cooled to ambient temperature and extracted with methylene chloride, dried with sodium sulfate, and concentrated under reduced pressure to yield a brown solid. Dilution of this solid with methanol (100 ml) and filtration yields 31.57 g of pure title product. Melting point is 132°–134° C. Silica gel TLC Rf is 0.46 in hexane and ethyl acetate (1:3). Infrared absorptions are observed at 3140, 3120, 1690, 1620, 1590, 1545, 1485, 1385, 1365, 1345, 1210, 1025, 1070, 1055, and 1035 cm$^{-1}$. NMR absorptions are observed at 7.18, 7.20–7.55, 7.0, 6.08, 4.15, 4.05, and 3.98$\delta$ (deuterochloroform solvent). The mass spectrum exhibits peaks at 368, 260, 259, 258, 231, and 216. Carbon:hydrogen:sulphur ratio is 64.98:4.24:8.56.

Following the procedure of Example 4, but employing the appropriate methyl 2-phenyl(thio)alkylacetate in place of methyl 2-(phenylthio)acetate, there are prepared the corresponding formula XXIIV products wherein $R_{12}$ is phenylthiomethyl.

Example 5—7-Isopropyl-4,9-dimethoxyfurochromone
(Formula XXIV of Chart A: $R_3$ and $R_4$ are both methoxy and $R_{12}$ is isopropyl)

To a mixture of the title product of Example 1 (50 g) and methyl isopropylcarboxylate (300 ml) under a nitrogen atmosphere is added sodium hydride (40 g as a 50% oil dispersion) over a period of 25 min. When evolution of hydrogen gas ceases, the reaction mixture is then heated at reflux for 22 hr and thereafter cooled to ambient temperature. Quenching (destroying sodium hydride) with water and diluting with diethyl ether yields a 2-phase system from which the aqueous phase is separated and washed with diethyl ether (200 ml). The aqueous phase is then acidified with 25% aqueous hydrochloric acid and extracted with diethyl ether (400 ml). The combined ethereal extracts are then dried over magnesium sulfate and concentrated under reduced pressure to yield a light brown oil. The oil is then diluted with methanol (300 ml) and anhydrous hydrochloric acid, which is bubbled through the methanolic solution. The methanolic solution is then refluxed for 2 hr, cooled to ambient temperature, diluted with water (200 ml), and extracted with methylene chloride (400 ml). The combined organic extracts are then dried over magnesium sulfate and concentrated under reduced pressure to yield a light tan oil which is recrystallized from ethyl acetate and hexane, yield 34.3 g of essentially pure title product. Melting point is 116°118° C.

Chromatographing a 16.0 g sample of the essentially pure product on 1.35 kg of silica gel packed in hexane and ethyl acetate (1:1) and eluting with this solvent yields 13.98 g of pure title product. Silica gel TLC Rf is 0.66 in hexane and ethyl acetate (1:1). Infrared absorptions are observed at 3130, 3100, 1650, 1625, 1595, 1540, 1480, and 1075 cm$^{-1}$. NMR absorptions are observed at 7.64, 7.0, 6.07, 4.15, 4.01, 2.90, and 1.31$\delta$ (deuterochloroform solvent). The mass spectrum exhibits peaks at 288, 273, 259, 245, 244, 217, 215, and 177. The carbon:hydrogen ratio is 66.73:5.52.

Following the procedure of Example 5, but employing the appropriate methyl alkanoate in place of methyl 2-methylpropionate, there are obtained the corresponding formula XXIV compounds wherein $R_{12}$ is alkyl.

Example 6—7-Cyclopropyl-4,9-dimethoxyfurochromone
(Formula XXIV of Chart A: $R_3$ and $R_4$ are both methoxy and $R_{12}$ is cyclopropyl.

Following the procedure of Example 5, employing methyl cyclopropanecarboxylate (75 g) in place of methyl cyclopropanecarboxylate, the title product of Example 1 (15 g) is transformed to 8.60 g of pure crystalline title product. Melting point is 135°–137° C. Silica gel TLC Rf is 0.55 is hexane and ethyl acetate (1:1). Characteristic infrared absorptions are observed at 3130, 3100. 1650, 1625, 1595, 1540, and 1480 cm$^{-1}$. NMR absorptions are observed at 7.62, 7.0, 6.1, 4.13, 4.02, 1.7–2.11, and 0.98–1.28$\delta$ (deuterochloroform solvent). The mass spectrum exhibits peaks at 286, 271, 237, 243, 215, 177, 149, and 147. Carbon:hydrogen ratio is 67.00:4.86.

Following the procedure of Example 6, but employing the appropriate methyl cycloalkanecarboxylate in place of methyl cyclopropanecarboxylate, there are prepared the corresponding formula XXIV compounds wherein $R_{12}$ is cycloalkyl.

Example 7—7-Undecyl-4,9-dimethoxyfurochromone (Formula XXIV of Chart A: $R_3$ and $R_4$ are both methoxy and $R_{12}$ is n-undecyl)

To a mixture of the title product of Example 1 (60 g.) and ethyl laurate (500 g) under nitrogen atmosphere is added sodium hydride (45 g in a 50% oil dispersion) over a period of 30 min. After addition of sodium hydride is complete, the reaction mixture is heated to 80° C. for 1.5 hr and thereafter cooled to ambient temperature. After solidification of a light brown mass, water (dropwise) and diethyl ether (500 ml) is employed to quench the reaction mixture. Thereafter additional water (for a total of 200 ml) is carefully added and the aqueous layer separated. The aqueous layer is then washed with diethyl ether and thereafter diluted with chloroform (300 ml) and acidified with 25% aqueous hydrochloric acid. The chloroform layer is then separated and the aqueous layer extracted with chloroform (100 ml) and the combined organic phase is then dried and filtered. After drying, anhydrous hydrochloric acid is passed through the chloroform solution for several minutes and the solution is refluxed for one hr. After cooling to ambient temperature the chloroform is then removed under reduced pressure yielding a brown oil (95.32 g) which solidifies.

Chromatographing of a 5 g sample of the oil on 250 g on silica gel packed with ethyl acetate and hexane (1:1) yields 2.35 g of pure title product. Melting point is 78°–79° C. Silica gel TLC Rf is 0.73 in hexane and ethyl acetate (1:1). Infrared absorptions are observed at 3120, 3060, 1660, 1555, 1485, 1375, 1360, 1125, 1095, 845, 765, and 720 cm$^{-1}$. NMR absorptions are observed at 7.65, 7.03, 6.1, 4.2, 4.08, 2.65, 1.05–1.90 and 0.87δ (deuterochloroform solvent). The mass spectrum exhibits peaks at 400, 386, 385, 371, 357, 329, 315, 229, 177, 105, 43, and 41. The carbon:hydrogen ratio is 71.88:8.27.

Following the procedure of Example 7, but employing the appropriate ethyl alkanoate in place of ethyl laurate, there are prepared each of the corresponding formula XXIV products wherein $R_{12}$ is alkyl.

Example 8—7-Trifluoromethyl-4,9-dimethoxyfurochromone (Formula XXIV of Chart A: $R_3$ and $R_4$ are both methoxy and $R_{12}$ is trifluoromethyl)

To sodium hydride (40.51 g of a 50% dispersion in oil) is added a mixture of the title product of Example 1 (50 g) and ethyltrifluoroacetate (90 g) under a nitrogen atmosphere. After addition is complete, the resulting mixture is stirred an additional 30 min at ambient temperature. Thereafter the reaction mixture is carefully quenched with water (200 ml), followed by addition of diethyl ether (500 ml). The aqueous phase is then separated and washed with diethyl ether (500 ml), diluted with chloroform, and acidified with 10% aqueous hydrochloric acid. The chloroform layer is then separated, and the aqueous layer extracted with chloroform (100 ml). The combined organic phases are then dried with magnesium sulfate and filtered. Anhydrous hydrochloric acid is then passed into the chloroform solution for several minutes, followed by refluxing for 45 min. The resulting mixture is then allowed to cool at ambient temperature and the solvent removed under reduced pressure, yielding a dark brown solid. After washing with diethyl ether (200 ml), there is obtained 35.26 g of pure title product. Recrystallization from ethyl acetate in hexane yields a product with melting point 266°–268° C. Silica gel TLC Rf is 0.57 in 5% ethyl acetate in chloroform. Infrared absorptions are observed at 3130, 1665, 1650, 1550, 1480, 1270, 1215, 1185, 1145, 1135, 1070, 950, and 870 cm$^{-1}$. NMR absorptions are observed at 7.69, 7.05, 6.60, 4.21, and 4.03δ (deuterochloroform solvent). The mass spectrum exhibits peaks at 314, 299, 285, 271, 270, 243, 215, 200, 120, and 105. The carbon-hydrogen-fluorine ratio is 53.77:2.92:18.08.

Following the procedure of Examples 2–8, each of the various formula XXIV compounds of Chart A is prepared from the title product of Example 1 and the appropriate carboxylic acid ester.

Example 9—1-(6-Hydroxy-4,7-dimethoxy-benzofuranyl)-3-(1-pyrrolidinyl)-2-buten-1-one (Formula XXV of Chart A: $R_3$ and $R_4$ are both methoxy and $R_{12}$ is methyl).

A methanolic solution of khellin (5.2 g) and pyrrolidine (2.82 g) is heated at 80° C. for 6 hr. Upon cooling, bright orange crystals precipitate from the reaction mixture. After filtration, there is obtained 6.3 g of pure title product. Silica gel TLC Rf os. 0.74 in ethyl acetate. Infrared absorptions are observed at 3180, 3160, 3120, 2300, 1630, 1600, 1530, 1345, 1325, 1260, 1170, 1155, 1140, 1130, 1060, 1050, and 1030 cm$^{-1}$. NMR absorptions are observed at 7.45, 6.8, 6.15, 4.05, 3.89, 3.22–3.70, 2.68, and 1.8–2.15δ. The mass spectrum exhibits peaks at 331, 300, 261, 220, 205, 177, 111, 110, 83, and 70. The carbon:hydrogen:nitrogen ratio is 65.09:6.32:4.18.

Following the procedure of Example 10, but employing each of the various formula XXIV 4,9-dimethoxy-7-substituted furochromones, there are prepared each of the various corresponding formula XXV products.

Example 10—6-Bromo-7-methyl-4,9-dimethoxyfurochromone (Formula XXVI of Chart A: $R_3$ and $R_4$ are both methoxy and $R_{12}$ is methyl)

To a chloroform (20 ml) solution of the title product of Example 9 (1.10 g) at 0° C. is added dropwise a chloroform (5 ml) solution of bromine (528 mg). After the addition of bromine is complete, the reaction mixture is diluted with water (50 ml) and stirred vigorously for 5 min. The chloroform layer is then separated and the aqueous layer extracted with chloroform (25 ml). The combined organic extracts are then dried over sodium sulfate and concentrated under reduced pressure to yield 1.2 g of a dark green material. This material is then chromatographed on 50 g of silica gel packed and eluted with 10% ethyl acetate and chloroform. Fractions containing pure title product (480 mg) are combined. Melting point is 176°–177° C. Silica gel TLC Rf is 0.70 in ethyl acetate. Infrared absorptions are observed at 3120, 1650, 1640, 1625, 1610, 1590, 1550, 1540, 1480, 1250, 1330, 1265, 1070, 1050, 870, 785, and 770 cm$^{-1}$. NMR absorptions are observed at 7.65, 7.01, 4.2, 4.04, and 2.65δ (deuterochloroform solvent). The mass spectrum exhibits peaks at 340, 338, 325, 323, 296, 295, 294, 279, 277, 250, 177, and 175. The carbon:hydrogen:bromine ratio is 49.74:3.36:23.57.

Following the procedure of Example 5, but employing in place of the title product of Example 9, each of the various corresponding formula XXV compounds described following Example 9, there are prepared each of the corresponding formula XXVI 6-bromofurochromones in accordance with the instant specification.

Further following the above procedures but employing the appropriate halogen other than bromine, there are prepared the various formula XXVI 6-chlorofurochromones or 6-iodofurochromones in accordance with the instant specification.

Example 11—6-Bromo-4,9-dimethoxyfurochromone (Formula XXXIII of Chart B: $R_3$ and $R_4$ are methoxy)

A. 1-(6-Hydroxy-4,7-dimethoxy-5-benzofuranyl)-3-dimethylamino-2-propen-1-one. The title product of Example 1 (25 g) and N,N-dimethylformamide dimethylacetal (13.7 g) are heated in an oil bath for 2.5 hr. The reaction product then precipitates and is cooled to ambient temperature. Excess methanol is then removed under reduced pressure and the resulting solid crystallized from methanol to yield 23.2 g of product. Melting point is 137°–139° C. Silica gel TLC Rf is 0.12 in hexane and ethyl acetate (1:1). Infrared absorptions are observed at 1625, 1555, 1535, 1500, 1265, 1060, 875, 770, and 730 cm$^{-1}$. NMR absorptions are observed at 8.00, 7.47, 6.82, 6.30, 4.05, 3.90 and 2.8–3.31$\delta$ (deuterochloroform solvent). The mass spectrum exhibits peaks at 291, 221, 220, 206, 205, 177, 163, and 98. Carbon:hydrogen:nitrogen ratio is 61.65:6.12:4.90.

B. 6-Bromo-4,9-dimethoxyfurochromone. To a chloroform (20 ml) solution of the reaction product of Part A (1.0 g) is added dropwise a chloroform (7 ml) solution of bromine (549 mg). After the bromine discolors, the reaction mixture is diluted with water (50 ml) and vigorously stirred for 5 min. Thereafter the chloroform layer is separated and the aqueous layer extracted with chloroform (50 ml). The combined chloroform extracts are then dried over sodium sulfate and concentrated under reduced pressure to yield a light yellow oil (825 mg). Chromatographing on 60 g of silica gel packed and eluted with 10% ethyl acetate in chloroform yields 640 mg of pure title product. Melting point is 166°–167° C. Silica gel TLC Rf is 0.60 in 10% ethyl acetate and chloroform. Infrared absorptions are observed at 3150, 3120, 2080, 1660, 1615, 1590, 1550, 1480, 1350, 1310, 1225, 1145, 1070, 1040, and 770 cm$^{-1}$. NMR absorptions are observed at 8.22, 7.71, 7.06, 4.28, and 4.11$\delta$. The mass spectrum exhibits peaks at 326, 324, 311, 309, 297, 295, 284, 282, 281, 280, and 53. Carbon:hydrogen-bromine ration is 43.22:2.70:24.57.

Following the procedure of Example 11, but employing the appropriate halogen other than bromine, there are prepared the various formula XXXIII compounds wherein X is chloro or iodo.

EXAMPLE 12—6-Chloro-4,9-dimethoxyfurochromone (Formula XXXIII of Chart B: $R_3$ and $R_4$ are methoxy)

The reaction product of Example 11, Part A (5.0 g) in chloroform (100 ml) is cooled to 0° C. and treated dropwise with a chloroform solution of t-butyl hypochlorite (1.85 g in 10 ml of chloroform) over 3 minutes with vigorous stirring. Thereafter, anhydrous hydrochloride is bubbled through the solution causing the reaction mixture to become a dark brown color. After stirring for an additional 2.5 hr, water, (58 ml) is added and stirring is continued for an additional 45 min. Thereafter the organic layer is separated, washed with brine, dried over magnesium sulfate, and concentrated under reduced pressure to yield 3.83 g of a dark brown solid. Successive recrystallizations from methanol yield 1.75 g of pure title product. Melting point is 178°–179° C. Silica gel TLC Rf is 0.57 in ethyl acetate and chloroform (1:9). Infrared absorptions are observed at 3150, 3120, 1660, 1615, 1590, 1550, 1480, 1350, 1310, 1145, 1070, 1040, and 770 cm$^{-1}$. NMR absorptions are observed at 8.1, 7.65, 7.02, 4.20, and 4.02$\delta$ (deuterochloroform solvent). The mass spectrum exhibits peaks at 282, 280, 267, 265, 251, 247, 246, 222, 209, 181, 177. Carbon:hydrogen:chlorine ratio is 55.64:3.41:12.52.

Example 13—4,9-Dimethoxy-7-methyl-6-methylthiomethyl furochromone (Formula LIII of Chart D: $R_3$ and $R_4$ are methoxy and $R_{10}$ is methyl)

A. [(4,9-Dimethoxy-5-oxy-5H-furo[3,2-g]-benzopyran-7yl)-methyl]dimethyl sulfonium fluorosulfate. (Formula LII)

To a solution of the title product of Example 3, (3.06 g, 10 mmole) in methylene chloride (50 ml) is added dropwise methylfluorosulfonate (1.14 g, 10 mmole) in methylene chloride (15 ml) over approximately 30 min at ambient temperature. The reaction is allowed to stir an additional 30 min, during which time a precipitate develops. The reaction is filtered, giving 2.78 g (66%) of a tan solid having a melting point of 193°–195° C. The carbon:hydrogen:sulfur analysis is 46.01:4.37:15.28. NMR absorptions are observed at 7.82, 7.10, 6.40, 4.85, 4.20, 4.00, and 3.15$\delta$. Infrared absorptions are observed at 3120, 2080, 1665, 1635, 1605. 1555. 1480, 1350, 1295, 1205, 1124, 1085, and 1070 cm$^{-1}$.

B. 4,9-Dimethoxy-6-methylthiomethyl-7-methylfurochromone

To a tetrahydrofuran solution (150 ml) of potassium tert-butoxide (1.26 g, 12.2 mmole) is added the reaction product, Part C, (5.14 g, 12.2 mmoles). Ten ml of water is then added to this heterogenous solution. The reaction first turns pink, then red, and after stirring overnight, yellow. The reaction is poured into methylene chloride (250 ml) and the resulting solution is washed with 5% hydrochloric acid (3×100 ml). The methylene chloride solution is dried over magnesium sulfate and the solid is removed in vacuo to give 3.59 of a light tan solid. The tan solid is chromatographed over 200 g of silica gel packed in 10% EtOAc/CHCl$_3$. Two 100 ml fractions are collected. Fractions 2 and 3 are combined to give 3.39 g (87%) of the desired product having a melting point of 1.51°–1.52° C. Carbon:hydrogen:sulfur analysis is 60.00:4.92:9.89. The mass spectrum exhibits peaks at 320, 305, 290, 275, 273, 259, 205, and 177. NMR absorptions are observed at 7.65, 7.03, 4.18, 4.02, 3.68, 2.5, and 2.15$\delta$. Infrared absorptions are observed at 3120, 3100, 1630, 1615, 1600, 1545, 1485, 1270, 1135, 1265, and 780 cm$^{-1}$.

Following the procedure in Example 13 each of the various Formula LIII compounds is prepared from the corresponding thio ether of formula LI.

Example 14—4,9-Dimethoxy-7-methyl-6-methylsulfinylmethyl-furochromone. (Formula LIV of Chart D: $R_3$ and $R_4$ are methoxy and $R_{11}$ is —CH$_2$—SO—CH$_3$)

Reaction product of Example 13 (32.0 g, 0.1 mole) is added to 1 l of CH$_2$Cl$_2$ with stirring. To this solution is added m-CPBA (20.23 g in 200 ml of CH$_2$Cl$_2$) dropwise over a 10 min period. The reaction is stirred at room temperature for 2 hr and then diluted with a saturated NaHCO$_3$ solution (300 ml) and vigorously stirred for 15 min. The CH$_2$Cl$_2$ solution is separated and the aqueous extracted with $CH_2Cl_2$ (200 ml). The combined organic material is dried over magnesium sulfate and the solvent is removed in vacuo to give 31.53 g of product. Chromatography of 20 g of this product over 2.1 kg of silica gel yields 9.75 g of pure title product with a melting point of 190°–191° C. Carbon:hydrogen:sulfur analysis is 57.35:4.98:9.36. The mass spectrum exhibits peaks at 336, 305, 274, 273, 258, 243, 230, 220, 205, 191, 177, and 53. NMR absorptions are observed at 7.65, 7.02, 4.19, 4.04, 3.98, and 2.62δ. Infrared absorptions are observed at 3130, 3100, 3070, 1630, 1620, 1595, 1550, 1485, 1365, 1270, 1120, 1065, and 1050 cm$^{-1}$.

Following the procedure of Example 14, but employing each of the various formula LIII 6-alkylthiomethylfurochromones, there are prepared each of the various corresponding formula LIV sulfinyl products.

Example 15—4,9-Dimethoxy-7-methyl-6-methylsulfonylmethylfurochromone (Formula LIV of Chart D: $R_3$ and $R_4$ are methoxy and $R_{11}$ is $-CH_2-SO_2-CH_3$)

The reaction product of Example 13 (10 g, 31.2 mmoles) is added to $CH_2Cl_2$ (500 ml). To this solution at room temperature is added a $CH2CL_2$ (200 ml) solution of m-CPBA (13.15 g) over a 15 min period. The reaction warms up slightly. The reaction is stirred a total of 30 min. A saturated $NaHCO_3$ solution (100 ml) is added to the reaction and stirring continues for approxiamtely 15 min. The material is then poured into a separatory funnel and the organic layer is separated. The aqueous layer is extracted with $CH_2Cl_2$ (50 ml) and the combined $CH_2Cl_2$ solution dried over magnesium sulfate and the solvent is removed in vacuo to give a light yellow solid. This material is completely homogeneous via TLC and after several washings with ether and yields 10.44 g (95%) of the title product having a melting point of 237°–239° C. Carbon:hydrogen:sulfur analysis is 54.34:4.69:9.36. The mass spectrum exhibits peaks at 352, 274, 273, 272, 230, 220, 205, 177, and 53. NMR absorptions are observed at 7.80, 7.0, 4.32, 4.02, 3.85, 2.85, and 2.47δ. Infrared absorptions are observed at 3150, 3120, 1635, 1625, 1595, 1550, 1485, 1365, 1300, 1190, 1140, 1115, and 1065 cm$^{-1}$.

Following the procedure of Example 15, but employing each of the various formula LIII 6-alkylthiomethylfurochromones there are prepared each of the various corresponding formula LIV products.

Example 16—4,9-Dimethoxy-7-(4-morpholinomethyl)furochromone (A formula XXIV of Chart A: $R_3$ and $R_4$ are methoxy and $R_{12}$ is 4-morpholinomethyl)

A 5 l flask equipped with a mechanical stirrer, condenser and nitrogen inlet is charged with NaH (41 g, 50% in oil, 0.85 moles) and 400 ml of hexane. This mixture is stirred for 5 min and then is allowed to settle. The solvent is removed via a gas dispersion tube. The residual gray solid is then suspended in dry THF (25 ml) in a solution of khellinone (formula XXII), the reaction product of Example 13, Part A, (50 g, 0.211 moles) and ethyl morpholinoacetate (76 g, 0.439 moles) and 200 ml of dry THF is added dropwise. Gas evolution is initially slow and heat is used to initiate the reaction. Thereafter the addition continues to be mildly exothermic. After 1 hr the addition is complete and dry dimethylacetamide (5 ml) is added. The resulting mixture is heated to reflux for 2 hr, then allowed to cool to room temperature. Cautiously, the cool reaction mixture is quenched with ice water (200 ml) and is concentrated in vacuo to a black syrup which is diluted with water to about 1 l, giving a homogenous solution. The solution is extracted with ether (2×150 ml) and the ethereal extracts are discarded. The aqueous mixture is treated sequentially with methanol (250 ml) and concentrated HCl (125 ml) to pH1. After several hours, the paste-like mixture is filtered and the solid washed with water (50 ml) and acetone (200 ml). After air drying the solid is taken up in $CHCl_3$, (800 ml) saturated with anhydrous HCl and heated to reflux for one hr. The two-phase mixture is then allowed to cool to room temperature and then washed with 2 N NaOH (3×100 ml). The combined basic washes are backwashed once with $CHCl_3$ and the total organic extracts are combined, dried ($Na_2SO_4$) and stripped in vacuo to a solid residue, 29 g. The residue is recrystallized from EtOAc/hexane to afford 26 g of pure product having a melting point of 117°–118° C. with a 35% yield. Carbon:hydrogen:nitrogen analysis is 62.62:5.59:4.05. The mass spectrum exhibits peaks at 346, 345, 330, 316, 272, 259, 231, 216, 201, and 100. NMR absorptions are observed at 7.69, 7.07, 6.37, 4.22, 4.01, 3.78, 3.55, and 2.65δ. Infrared absorptions are observed at 3120, 3100, 3060, 1650, 1630, 1615, 1550, 1480, 1365, 1345, 1.115 and 1075 cm$^{-1}$.

Example 17—4,9-Dimethoxy-7-(4-morpholinomethyl)furochromone-(Z)-2-butenedionate

The reaction product of Example 16 (3.23 g, 9.36 mmoles) is suspended in dry methanol (30 ml) and a solution of maleic acid (1.09 g, 9.36 mmoles) in methanol (20 ml) is added all at once. A clear solution results, and a precipitate appears after 2 min. After 5 min total, the mixture is diluted with 25 ml of ether and the precipitate is collected on a filter. This crystalline solid is then recrystallized from methanol-ether to afford a 3.55 g (7.7 mmoles) of pure maleate salt. Melting point 162°–164° C. (82% yield). Carbon:hydrogen:nitrogen analysis is found to be 57.20:4.94:3.04. NMR absorptions are observed at 7.85, 7.11, 6.28, 6.24, 5.67, 4.19, 4.01, 3.75, and 2.70δ. Infrared absorptions are observed at 3150, 3120, 1260, 1990, 1930, 1705, 1665, 1645, 1620, 1565, 1545, 1480, 1385, 1360, 1125, 1075, 1060, and 870 cm$^{-1}$.

Following the procedure of Example 17 various acid addition salts are prepared from the corresponding acids.

Example 18—4,9-Dimethoxy-7-(piperidinylmethyl)furochromone (formula LXV of Chart A; $R_3$ and $R_4$ are methoxy and $R_{12}$ is piperidinylmethyl)

A three-liter flask is equipped with a mechanical stirrer, condenser and nitrogen inlet and charged with NaH (39.1 g of 50% in oil, 0.81 moles). Hexane (250 ml) is added and the NaH is suspended for 5 min, then allowed to settle. The supernatant is removed via a gas dispersion tube and the residual dry NaH is suspended in dry THF (25 ml) with stirring. To this suspension is added a warm solution of khellinone (formula XXII), the reaction product of Example 13, Part A, (45.8 g, 0.194 moles) and ethyl piperidinoacetate (69.7 g, 0.40 moles) in the THF (150 ml) dropwise. After the first 10 ml of the solution are added to the NaH, the reaction is initiated with heat. The rate of addition is such that a gentle reflux is maintained. After the addition is complete, the resultant mixture is heated to reflux for 2.5 hr, then cooled in ice water and quenched with water (200 ml). This aqueous solution is concentrated in vacuo to about ⅔ its volume, then diluted with 1 l of water and is extracted with ether (2×200 ml). The aqueous layer is acidified with concentrated hydrochloric acid to pH 1, diluted with methanol (125 ml) and is heated to reflux for 1.5 hr. Upon cooling, the mixture is taken to pH 8, using 6 N sodium hydroxide and is extracted with $CH_2Cl_2$ (3×300 ml). Evaporation of the extract in vacuo gives 27 g of bright yellow solid. The solid is suspended in $CHCl_3$ (850 ml) and dry HCl gas is bubbled for about 10 min. The resulting red-orange mixture is heated to reflux for 1.5 hr, then allowed to cool to room temperature and is extracted with 2 N sodium hydroxide. The $CHCl_3$ layer is dried over magnesium sulfate and evaporated to afford 27 g of crude oil. Upon two crystallizations from EtOAc/hexane (1:1.5) pure product was obtained (10 g), having a melting point of 84°–85° C. with a yield of 15%. Carbon:hydrogen:nitrogen analysis is found to be 66.49:6.02:4.15. The mass spectrum exhibits peaks at 344, 343, 328, 260, 231, and 98. NMR absorptions are observed at 7.65, 7, 6.30, 4.16, 4.04, 3.48, 2.50, and 1.52δ. Infrared absorptions are observed at 3120, 3100, 3060, 2740, 1650, 1635, 1620, 1595, 1550, 1480, 1385, 1365, 1340, 1130, 1075, and 1065 $cm^{-1}$.

Example 19—4,9-Dimethoxy-7-(N,N-dimethylaminomethyl)-furochromone (formula LXV of Chart A: $R_3$ and $R_4$ are methoxy and $R_{12}$ is N,N-dimethylaminomethyl)

A 5 l flask, equipped with mechanical stirrer, reflux condenser, and nitrogen inlet, is charged with NaH (61 g, 50% in oil, 1.27 moles) in hexane (600 ml). After stirring for 5 min, the suspended NaH is allowed to settle and the supernatant is removed via a gas dispersion tube. The residual solid is suspended in dry THF (30 ml) and a warm solution of khellinone (formula XXII) reaction product of Example 13, Part A, (74.4 g, 0.315 mole) in THF (200 ml) is added dropwise over 30 min. Then dimethylaminoglycine ethyl ester (82.2 g, 0.627 mole) is added in a thin stream. Reaction is initiated with heat causing vigorous foaming and refluxing. After about 10 min the reaction slows considerably and the mixture is heated to reflux for 5 hr. After cooling to ambient temperature, ice is added cautiously, then water (about 500 ml). This solution is extracted with ether (2×300 ml) and the ether extracts are discarded. The aqueous mixture is then treated with concentrated hydrochloric acid to pH 1 and allowed to stand overnight. The resulting yellow precipitate is collected, the filtrate is concentrated to about 200 ml in vacuo, and then filtered again. The collected solids are combined and washed with ether (200 ml) to yield 145 g of a yellow solid.

A portion (120 g) of this solid is taken up in $CHCl_3$ (1.2 l) and is treated with HCl gas for 4 min. The resulting red solution is heated to reflux for 1 hr, then is stirred at room temperature overnight. The $CHCl_3$ mixture is shaken with 2 N sodium hydroxide (2×300 ml), brine (1×100 ml) and dried over sodium sulfate.

The solvent is then removed under reduced pressure to afford 14 g of an impure product which is chromatographed over 1 kg of silica gel packed in 10% MeOH/$CHCl_3$. Fractions of 500 ml are collected. Fractions 5, 6, and 7 are combined. The residue from these fractions is recrystallized from EtOAc/hexane to yield 2.25 g of yellow prisms having a melting point of 108°–109.5° C., a 2.3% yield. Carbon:hydrogen:nitrogen analysis is found to be 63.63:5.66:4.66. The mass spectrum exhibits peaks at 304, 303, 288, 274, 243, 231, 84, 71, and 58. NMR absorptions are observed at 7.65, 7.03, 6.28, 4.19, 4.05, 3.45, and 2.38δ. Infrared absorptions are observed at 3120, 3080, 3060, 2790, 1650, 1630, 1620, 1595, 1545, 1485, 1385, 1075, and 1055 $cm^{-1}$.

Example 20—5β-Hydroxy-6,7-dihydro-4,9-dimethoxy-7-methyl-furochromone (Formula LXXII of Chart F: $R_3$ and $R_4$ are methoxy and $R_{14}$ is methyl)

In a 5 l flask fitted with addition funnel, mechanical stirrer, condenser is placed $NaBH_4$ (51.0 g, 1.36 mole) and 100 ml of EtOH. To this slurry is added a solution of khellin (51.7 g, 1.98 moles) and 4 l of warm EtOH in a thin stream. The addition of khellin takes 1.5 hr and the resulting mixture is heated to reflux for 4 hr. The solution is then allowed to cool and concentrated in vacuo to a thick paste which is treated with two liters of aqueous $NaHCO_3$ for 2 hr with vigorous stirring. This mixture is diluted with 1 l of water and 1 l of $CH_2Cl_2$ and stirred overnight. Layers are then separated and the aqueous phase extracted with $CH_2Cl_2$ (4×750 ml). The organic extracts are combined, shaken with brine (500 ml), filtered through $Na_2SO_4$ and concentrated in vacuo to a solid. This residue is taken up in 200 ml of hot EtOAc, quickly filtered and diluted with hexane (250 ml). On cooling, white crystals deposit weighing 20.7 g and having a melting point of 88°–90° C. The mother liquors afforded 8 g of additional material on cooling, having a melting point of 88°–91° C. and having a yield of 55%. Analytically pure material is prepared by recrystallization from ethanol-ether and has a melting point of 91°–92° C. Carbon:hydrogen ration is 63.63:6.06. NMR absorptions are observed at 7.46, 6.82, 5.22, 4.20, 4.10, 4.00, 3.80, 2.33, 1.92, and 1.50δ. Infrared absorptions are observed at 3546, 3133, 1626, 1598, 1555, 1487, 1257, 1141, 1091, 1060, and 1045 $cm^{-1}$.

Following the procedure of Example 23 but employing the various Formula LXXI 6,7-substituted furochromones previously described there are prepared the various formula LX compounds.

Example 21—4,8-Dimethoxybenzo[1,2-b; 5,4-b']difuran-3(2H)-one (Formula LXXIII of Chart E: $R_3$ and $R_4$ are methoxy)

A. (Z)-2-[(1-pyrrolidinyl)methylene]-4,8-dimethoxybenzo-[1,2-b;-5,4-b]difuran-3-(2H)-one (formula LXII) title compound, Example 11 (6.5 g, 20 mmoles) and potassium carbonate are added to $CH_3CN$ (200 ml). To this solution is added pyrrolidine (1.42 g, 20 mmoles) and the resulting solution is stirred at room temperature for 18 hr. The $CH_3CN$ is removed in vacuo to leave a yellow solid which is washed with water, filtered, and dried to give 3.19 g (54% yield) of the above product having a melting point of 216°–217° C. Carbon:hydrogen:nitrogen analysis ratio is 64.86:5.55:4.42. Mass spectrum exhibits peaks at 315, 301, 300, 286, 285, 231, 230, and 217. NMR absorptions are observed at 7.5, 7.19, 6.91, 4.29, 4.12, 3.72, 1.99. Infrared absorptions are observed at 3140, 3100, 1675, 1625, 1600, 1585, 1545, 1495, 1340, 1270, 1235, 1125, and 1065 $cm^{-1}$.

B. Reaction product of Part A (12.55 g, 39.8 moles) is added to 500 ml of a 1:1 mixture of tetrahydrofuran and 2 N HCl. This mixture is heated at reflux for 16 hr during which time the reaction turns dark red with a formation of a dark red solid. After cooling to room temperature, the solid is filtered to give 2.91 g of material (insoluble on both H₂O and CHCl₃). The filtrate is reduced in volume in vacuo to give a heterogeneous solution which is filtered to give 5.20 g of crude product. The filtrate is extracted with CH₂Cl₂ (4×75 ml) to give 710 mg of additional product. 5.91 g of the crude reaction is chromatographed over 250 g of HPLC silica gel packed in 20% EtOAc/CHCl₃ and gives 4.25 g (44% yield) of the title product having a melting point of 146°–148° C. Carbon:hydrogen ratio is 61.32:4.50. Mass spectrum exhibits peaks at 234, 220, 219, 205, 191, 176, 163, 153, and 77. NMR absorptions are observed at 7.47, 6.88, 4.67, 4.22, and 4.10δ. Infrared absorptions are observed at 3000, 2950, 2850, 1710, 1600, 1550, 1500, 1440, 1380, 1340, 1260, 1120, and 1060 cm⁻¹.

Following the procedure of the Examples above, but employing the appropriate desmethoxy starting materials (e.g., 4-desmethoxy khellin, of formula XXI wherein R₃ is hydrogen and R₄ is methoxy, or 9-desmethoxy khellin, formula XXI wherein R₄ is hydrogen and R₃ is methoxy), there are prepared the corresponding desmethoxy products of Charts A–F. Such desmethoxy starting materials are known in the art. For example, 4-desmethoxy khellin is described in U.S. Pat. No. 3,099,660 and 9-desmethoxy khellin is the naturally-occurring visnagin of formula III.

Accordingly there is provided by the Examples above methods for the preparation of each of the various formula VI furochromone analogs described herein.

FORMULAS

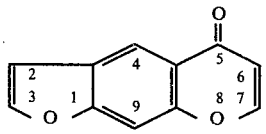  I

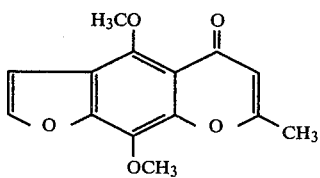  II

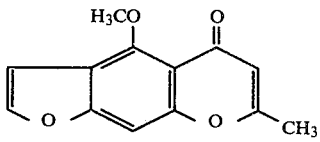  III

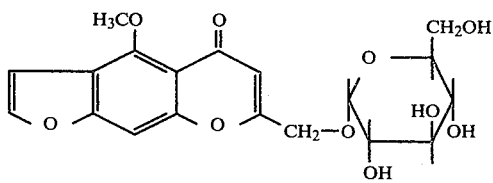  IV

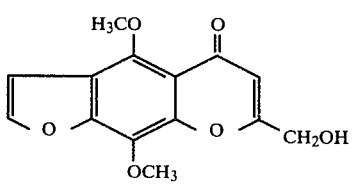  V

-continued
FORMULAS

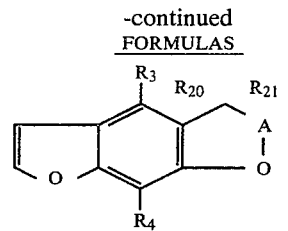  VI

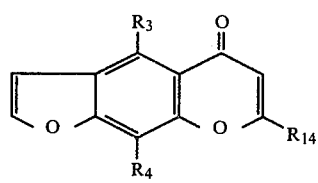  VII

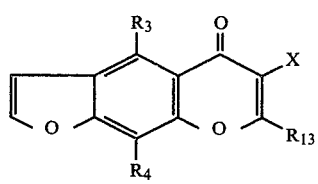  VIII

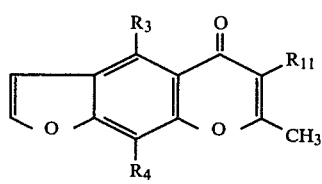  IX

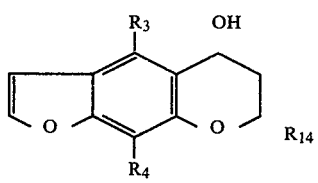  X

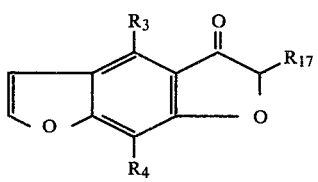  XI

CHART A

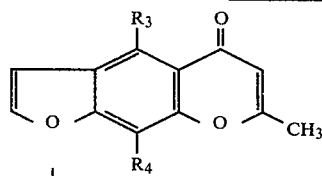  XXI

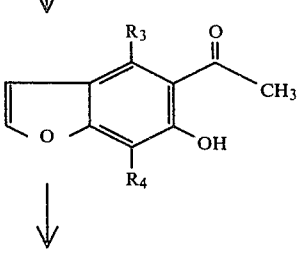  XXII

CHART A -continued

XXIII, XXIV, XXV, XXVI

CHART B

CHART C

XLI, XLII, XLIII

CHART D

LI, LII, LIII, LIV

CHART E

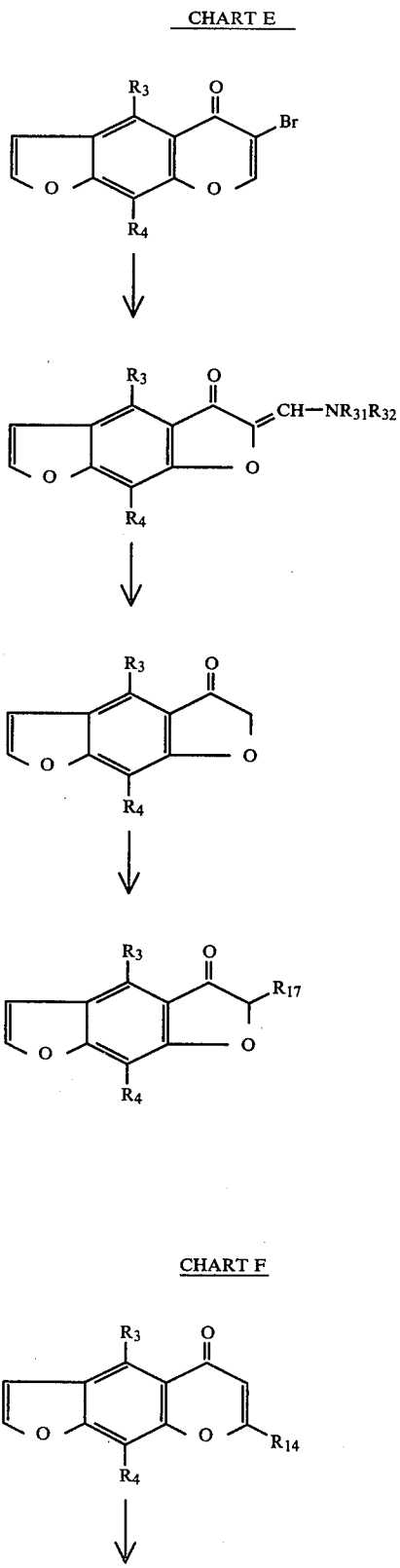

CHART F

-continued
CHART F

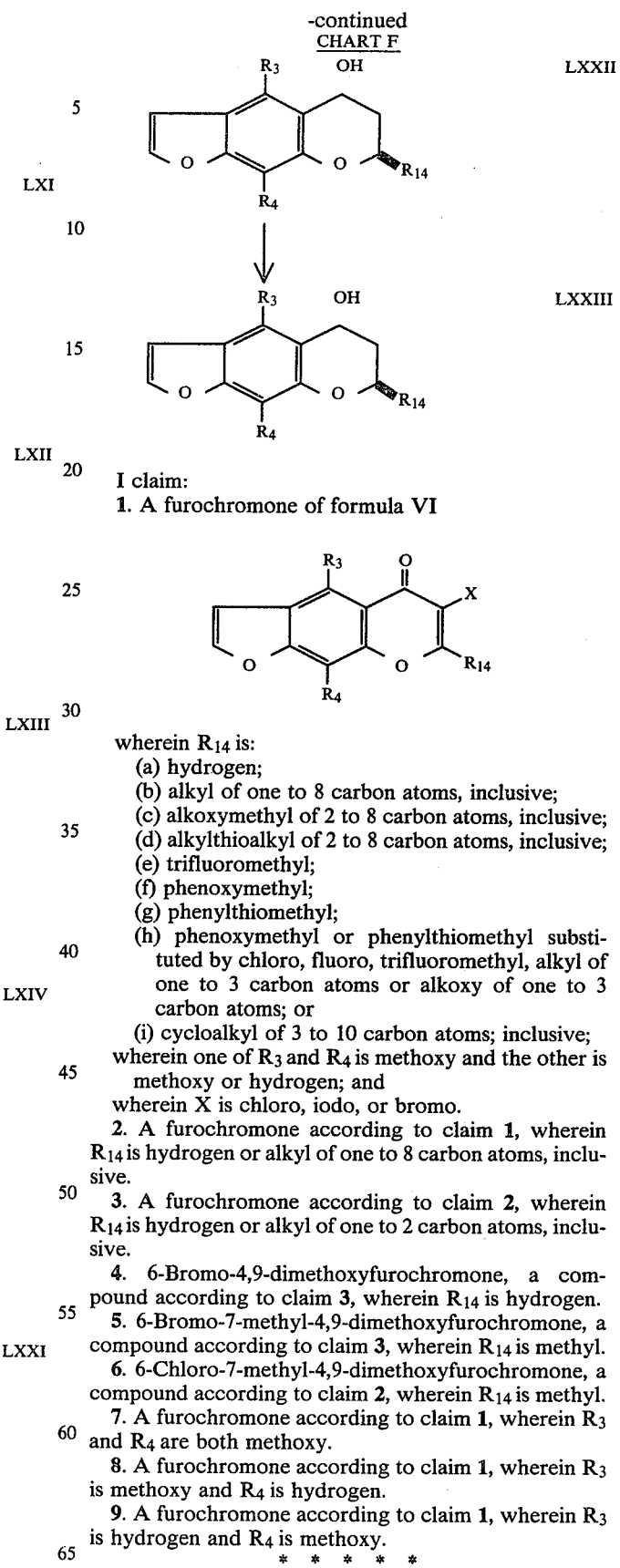

I claim:
1. A furochromone of formula VI wherein $R_{14}$ is:
 (a) hydrogen;
 (b) alkyl of one to 8 carbon atoms, inclusive;
 (c) alkoxymethyl of 2 to 8 carbon atoms, inclusive;
 (d) alkylthioalkyl of 2 to 8 carbon atoms, inclusive;
 (e) trifluoromethyl;
 (f) phenoxymethyl;
 (g) phenylthiomethyl;
 (h) phenoxymethyl or phenylthiomethyl substituted by chloro, fluoro, trifluoromethyl, alkyl of one to 3 carbon atoms or alkoxy of one to 3 carbon atoms; or
 (i) cycloalkyl of 3 to 10 carbon atoms; inclusive;
wherein one of $R_3$ and $R_4$ is methoxy and the other is methoxy or hydrogen; and
wherein X is chloro, iodo, or bromo.

2. A furochromone according to claim 1, wherein $R_{14}$ is hydrogen or alkyl of one to 8 carbon atoms, inclusive.

3. A furochromone according to claim 2, wherein $R_{14}$ is hydrogen or alkyl of one to 2 carbon atoms, inclusive.

4. 6-Bromo-4,9-dimethoxyfurochromone, a compound according to claim 3, wherein $R_{14}$ is hydrogen.

5. 6-Bromo-7-methyl-4,9-dimethoxyfurochromone, a compound according to claim 3, wherein $R_{14}$ is methyl.

6. 6-Chloro-7-methyl-4,9-dimethoxyfurochromone, a compound according to claim 2, wherein $R_{14}$ is methyl.

7. A furochromone according to claim 1, wherein $R_3$ and $R_4$ are both methoxy.

8. A furochromone according to claim 1, wherein $R_3$ is methoxy and $R_4$ is hydrogen.

9. A furochromone according to claim 1, wherein $R_3$ is hydrogen and $R_4$ is methoxy.

* * * * *

UNITED STATES PATENT AND TRADEMARK OFFICE
CERTIFICATE OF CORRECTION

PATENT NO. : 4,313,883
DATED : February 2, 1982
INVENTOR(S) : Ronald B. Gammill

It is certified that error appears in the above—identified patent and that said Letters Patent is hereby corrected as shown below:

Column 4, line 13; change "peealpha..." to ---peralpha...---.

Column 4, line 29; change "rad" to ---rat---.

Column 15, line 32; change "3060, 1660, 1555, ..." to ---3060, 1660, 1620, 1555...---.

Column 18, line 13; change "7y1)-" to ---7-y1)- ---.

Column 28, line 5; change " 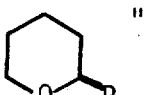 " to --- 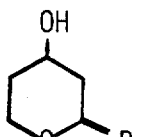 ---.

Column 28, line 15; change " 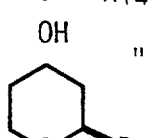 " to --- 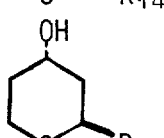 ---.

Signed and Sealed this

Twenty-sixth Day of October 1982

[SEAL]

Attest:

Attesting Officer

GERALD J. MOSSINGHOFF
Commissioner of Patents and Trademarks